(12) United States Patent
Brink

(10) Patent No.: US 7,860,565 B2
(45) Date of Patent: Dec. 28, 2010

(54) DEFIBRILLATOR HAVING A SWITCHED MODE POWER SUPPLY FOR TRANSCUTANEOUS PACING

(75) Inventor: Gregory D. Brink, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 854 days.

(21) Appl. No.: 11/575,775

(22) PCT Filed: Sep. 12, 2005

(86) PCT No.: PCT/IB2005/052984

§ 371 (c)(1),
(2), (4) Date: Mar. 22, 2007

(87) PCT Pub. No.: WO2006/035335

PCT Pub. Date: Apr. 6, 2006

(65) Prior Publication Data

US 2008/0065160 A1 Mar. 13, 2008

Related U.S. Application Data

(60) Provisional application No. 60/614,453, filed on Sep. 29, 2004, provisional application No. 60/651,433, filed on Feb. 8, 2005.

(51) Int. Cl.
*A61N 1/39* (2006.01)

(52) U.S. Cl. ........................................................ 607/4
(58) Field of Classification Search ...................... 607/4
See application file for complete search history.

(56) References Cited

U.S. PATENT DOCUMENTS

| 4,019,519 | A  | * | 4/1977 | Geerling ........................ 607/72 |
| 6,104,953 | A  | * | 8/2000 | Leyde ............................. 607/4 |
| 6,208,895 | B1 | * | 3/2001 | Sullivan et al. ................. 607/4 |
| 6,417,649 | B1 | * | 7/2002 | Brink ........................... 320/166 |

FOREIGN PATENT DOCUMENTS

WO          01/26731 A      4/2001

* cited by examiner

*Primary Examiner*—George R Evanisko
*Assistant Examiner*—Andrew Hayes
(74) *Attorney, Agent, or Firm*—W. Brinton Yorks, Jr.

(57) ABSTRACT

A defibrillator for providing both defibrillating energy and pacing energy to a patient is described. In delivering the defibrillating energy, electrical energy is stored by a charge capacitor and the stored energy is then coupled to the patient to provide a defibrillating pulse. To deliver pacing energy to a patient, an electrical energy circuit generates electrical energy that is filtered by the charge capacitor and delivered to the patient as pacing energy. The magnitude of the pacing energy delivered to the patient is monitored by a controller, which adjusts the generation of the electrical energy based on the magnitude of the pacing energy in order to provide adequate pacing energy to the patient.

18 Claims, 2 Drawing Sheets

DEFIBRILLATOR HAVING A SWITCHED MODE POWER SUPPLY FOR TRANSCUTANEOUS PACING

CROSS REFERENCE TO RELATED APPLICATION

This application claims the benefit of U.S. provisional application Ser. Nos. 60/614,453 and 60/651,433 filed Sep. 29, 2004 and Feb. 8, 2005, respectively, which are incorporated herein.

This invention relates generally to an apparatus and method for delivering therapeutic electrical energy to a patient, and more specifically, to apparatus for delivering both defibrillating and pacing energy to a patient.

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated that more than 1000 people per day are victims of SCA in the United States alone. SCA occurs when the heart stops pumping blood. Usually SCA is due to abnormal electrical activity in the heart, resulting in an abnormal rhythm (arrhythmia). One such abnormal rhythm, ventricular fibrillation ("VF"), is caused by abnormal and very fast electrical activity in the heart. During VF the heart cannot pump blood effectively. Because blood may no longer be pumping effectively during VF, the chances of surviving decrease with time after the onset of the emergency. Brain damage can occur after the brain is deprived of oxygen for four to six minutes. VF is treated by applying an electric shock to the patient's heart through the use of a defibrillator. The shock clears the heart of the abnormal electrical activity (in a process called "defibrillation") by depolarizing a critical mass of myocardial cells to allow spontaneous organized myocardial depolarization and a regular heartbeat to resume.

Other forms of abnormal cardiac rhythms which are generally not immediately life-threatening, such as bradycardia (slow heart rate) and tachycardia (rapid heart rate) can be treated with a low voltage pacing pulse, which assists the heart's natural pacemakers. Unlike a defibrillator, which applies pulses of several thousand volts over the usually short interval necessary to disrupt ventricular fibrillation, pacing pulses are generally continuously applied at much lower voltage levels over a sustained period of time. The demands placed on a pacemaker for long performance periods at lower voltages are thus incompatible with the aperiodic performance periods of a defibrillator at much higher voltage levels. While the similar functionality of the two devices, providing electrical therapy to the heart, makes a combined defibrillator/pacemaker monitor attractive, the dissimilar nature of the voltage levels, energy usage, and timeframes involved generally results in a combined device having separate circuitry for the two functions. This use of separate circuitry necessarily increases the weight, size, and cost of a combined defibrillator/pacemaker monitor. For example, currently available defibrillators with pacing capabilities typically include two power supplies, two capacitors, and two control mechanisms—one for the high voltage defibrillation pulse and one for the lower energy pacing pulses.

Despite these obstacles, fairly compact monitors having combined defibrillating and pacing features have been developed. For example, a compact device having both defibrillating and pacing features is described in U.S. Pat. No. 6,104,953 to Leyde. As described in the Leyde patent, a single power source is used for the delivery of either pacing or defibrillating energy. According to one embodiment described therein, a defibrillator includes a power source, a capacitor, and a control circuit for controlling the delivery of either high voltage defibrillation pulses or lower voltage pacing pulses from the capacitor to a patient. In the defibrillating mode a semiconductor device such as a GTO or an IGBT is operated as a switch during the production of high voltage defibrillating pulses. In the pacing mode, the capacitor is charged to a predetermined voltage level, such as 100-300 volts, and the energy stored by the capacitor is delivered through the semiconductor device operating in a linear mode as a control means for regulating the pacing current (which is in the range of 10-200 mA) applied to a patient. A sensing circuit is needed to sense the pacing current delivered and a control circuit is responsive to the sensed current to regulate the semiconductor device for the continuous application of the desired current. The use of a linear amplifier design such as in the defibrillator described in the Leyde patent can result in inefficient delivery of pacing current for most patients. As a result, the life of a battery providing energy for charging the capacitor for pacing purposes is compromised. Therefore, there is a need for a system capable of delivering either defibrillating or pacing pulses in a more efficient manner, and with significant circuit commonality so as to reduce the size, weight, and cost of the combined system.

The present invention is directed to a defibrillator that can deliver defibrillating pulses or pacing current waveforms to a patient. In an illustrated embodiment, a charging circuit charges a high voltage storage circuit for the delivery of high voltage defibrillating pulses. In the pacing mode, the operation of the charging circuit is controlled to charge the storage circuit to a lower voltage needed for pacing and the storage circuit functions to filter the charging current. The pacing current is sensed by a low voltage measurement circuit which controls the operation of the charging circuit. Many of the system components are thus used in both modes of operation, reducing much of the need for separate defibrillating and pacing circuitry.

Figure 1:
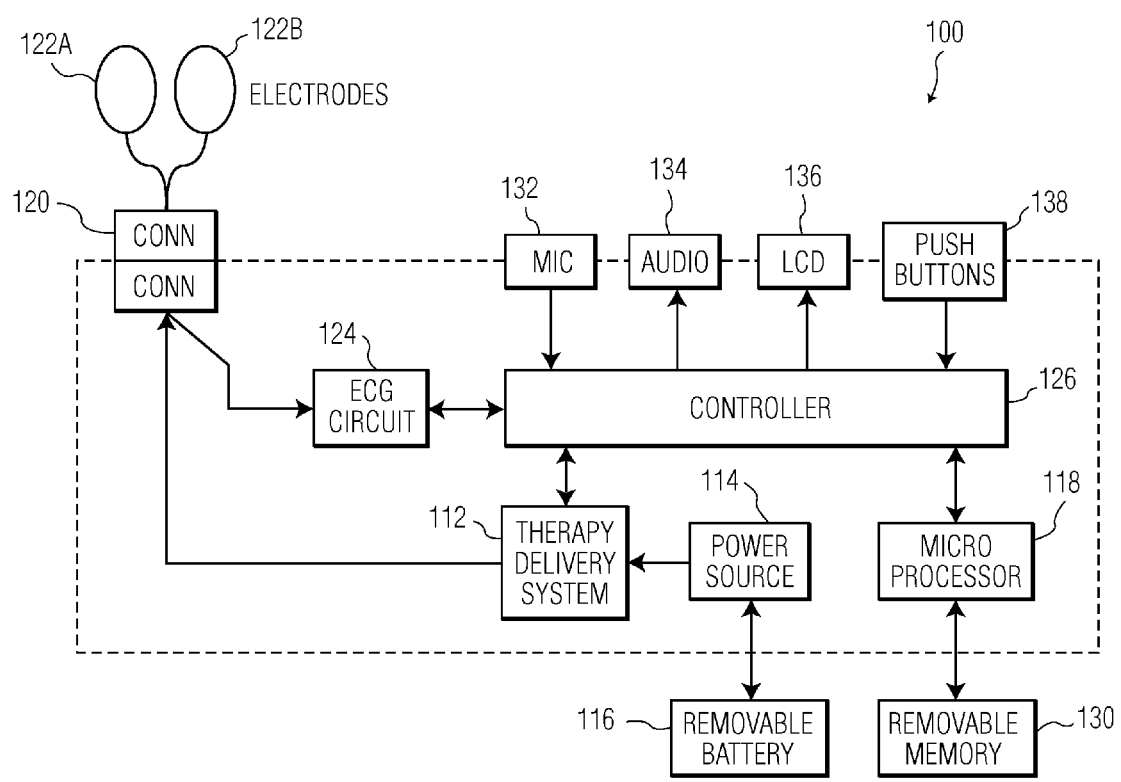
FIG. 1 is a functional block diagram of a defibrillator in which embodiments of the present invention may be utilized.

FIG. 1 illustrates a defibrillator 100 in which embodiments of the present invention can be utilized. The defibrillator 100 includes a therapy delivery system 112 capable of delivering a pulse of electrical energy to a patient through an electrode connector 120 and electrodes 122. As will be explained in more detail below, the therapy delivery system 112 can deliver high voltage defibrillating pulses or lower voltage pacing current to a patient. The defibrillator 100 further includes a power source 114 that is powered by an energy source such as a removable battery 116. The power source 114 provides power to the therapy delivery system 112, as well as to other components of the defibrillator 100. A microprocessor 118 for controlling the operation of the various components of the defibrillator 100 is also included in the defibrillator 100.

Coupled to the microprocessor 118 is a controller 126 for interfacing the microprocessor 118 with other components of the defibrillator 100. The controller 126 also controls many of the defibrillator functions, including user interface control and many of the internal functions of the defibrillator 100. The controller 126 can be implemented as a gate array, a custom application-specific integrated circuit (ASIC), or other control logic architecture as well as any combination thereof. Providing the separate controller 126 allows the microprocessor 118 to focus on other tasks. In alternative embodiments of the defibrillator, the functionality of the controller 126 can be included within the operations performed by the microprocessor 118, or can be replaced by discrete logic circuit components or a separately dedicated processor. An electrocardiogram (ECG) circuit 124 coupled to the controller 126 acquires and processes the patient's ECG signals through the electrodes 122 and sends the signals to the microprocessor 118 through the controller 126.

The defibrillator 100 further includes a memory device 130 (such as a removable Personal Computer Memory Card International Association ("PCMCIA") card, Secure Digital card, or flash memory), and user interface components such as a microphone 132, an audio speaker 134, an LCD display panel 136, and a set of push-button controls 138. It will be appreciated by those of ordinary skill in the art that a number of other components are included within the defibrillator 100, for example, a system monitor and associated status indicators, but are not shown in FIG. 1 in order to avoid unnecessarily obscuring the description of embodiments of the invention.

Figure 2:
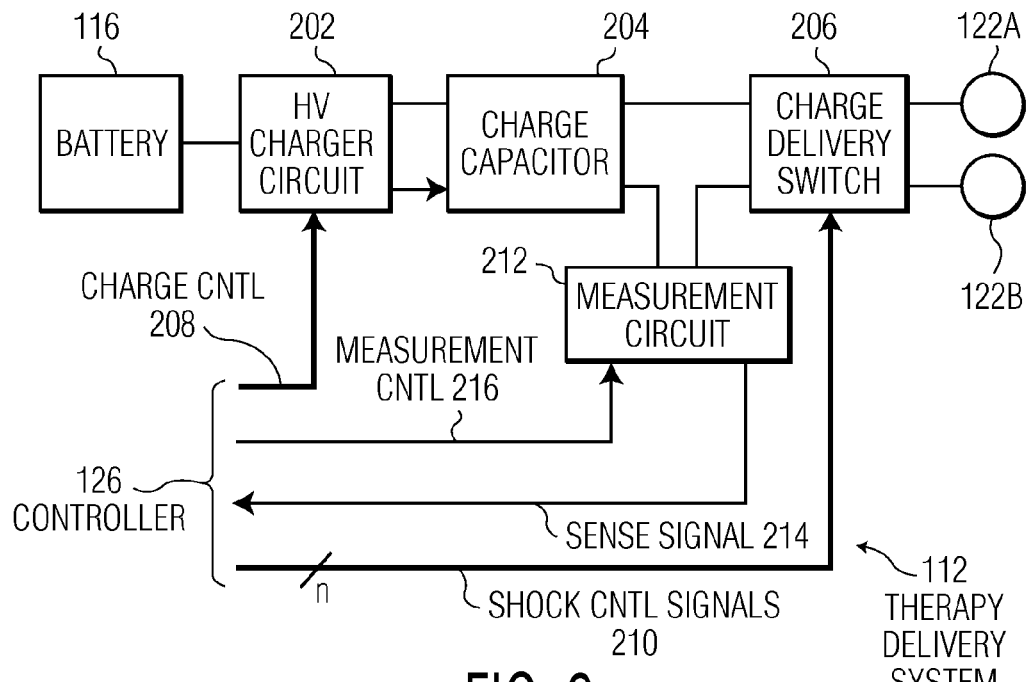
FIG. 2 is a functional block diagram of an energy delivery system according to an embodiment of the present invention.

FIG. 2 is a high-level functional block diagram of therapy delivery system 112 according to an embodiment of the present invention. In this embodiment the power source comprises a high voltage (HV) charger circuit 202 which is coupled to the battery 116. The HV charger circuit 202 is preferably a switched mode power supply having a flyback transformer configuration. An example of such a HV charger circuit is described in U.S. Pat. No. 6,417,649 to Brink, entitled SYSTEM AND METHOD FOR CHARGING A CAPACITOR USING A CONSTANT FREQUENCY CURRENT WAVEFORM, which is incorporated herein by reference. When the defibrillator 100 is in a defibrillating mode to provide defibrillating energy to a patient, the HV charger circuit 202 charges the capacitor 204 of therapy delivery system 112 in response to charge control commands 208 generated by the controller 126 (FIG. 1). The charge capacitor 204 includes a capacitor or a plurality of capacitors to store the high voltage defibrillation energy to be delivered to the patient. Preferably, the charge capacitor is charged to over 2,000 volts for delivery of 1100-1300 Joules of defibrillating energy. The delivery of energy stored in the charge capacitor 204 for defibrillation is controlled by a charge delivery switch 206. The charge delivery switch 206 delivers defibrillating pulses to the electrodes 122A and B in response to a shock control signals 210 from the controller 126.

The HV charger circuit 202 is further capable of providing pacing current through the charge delivery switch 206. As will be described in more detail below, the charge capacitor 204 is used as a filter during pacing with the HV charger circuit 202 providing the pacing current. The current output of the HV charger circuit 202 and capacitor 204 during pacing is monitored by a measurement circuit 212, which provides a sense signal 214 indicative of the magnitude of the pacing current. The sense signal 214 is provided to the controller 126, which in turn adjusts the output of the HV-charger circuit 202 to provide the desired level of pacing current. The measurement circuit 212 is coupled to the controller 126 to receive a measurement control signal 216 that controls whether the sense signal 214 is to be provided (during pacing) or the measurement circuit 212 is to be bypassed (during defibrillating).

Figure 3:
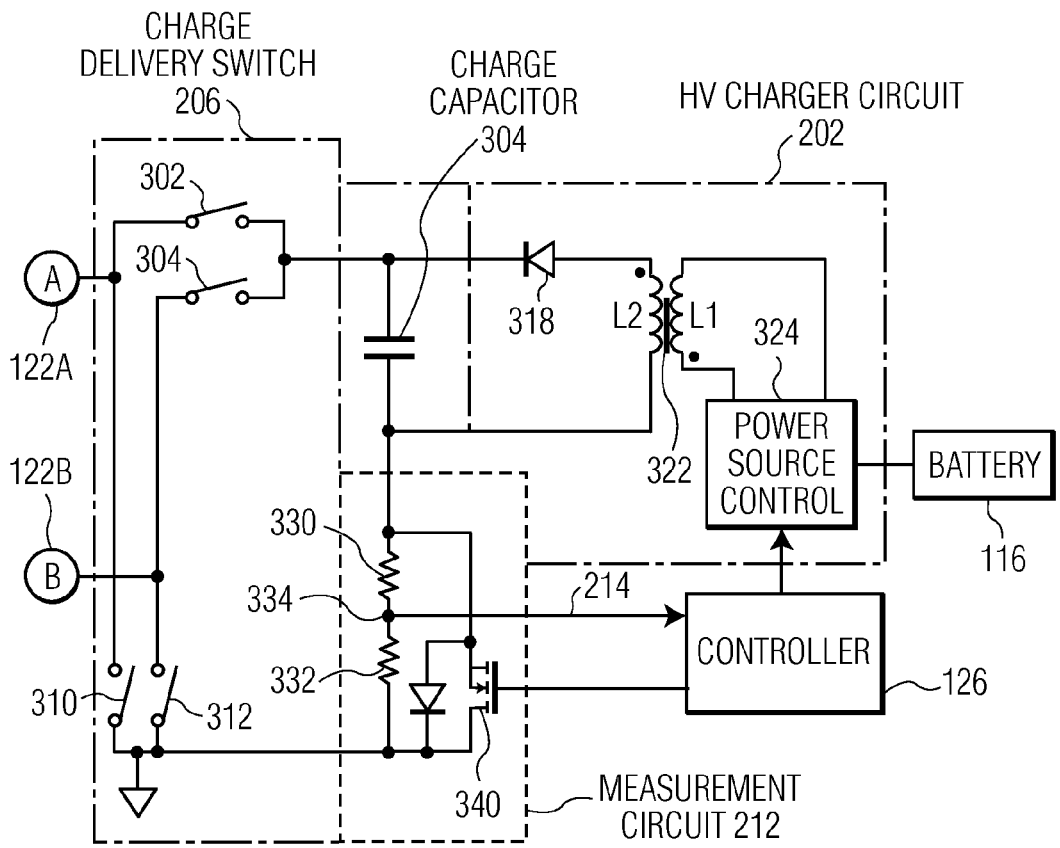
FIG. 3 is a schematic diagram of the energy delivery system illustrated in FIG. 2 according to an embodiment of the present invention.

FIG. 3 is a schematic block diagram of a defibrillator and pacing system according to an embodiment of the present invention. The HV charger circuit 202 includes a flyback transformer 322 with a primary coil L1 connected to a power source control circuit 324. The power source control circuit 324 is connected to the battery 116, which serves as a source of DC current. The power source control circuit 324 can be any well known power switch circuitry that provides an alternating current signal of a controllable duty cycle across the primary coil L1 of the transformer 322. Typically, the power source control circuit includes a field-effect transistor (FET) switch (not shown) to ground that applies a series of current pulses to the primary coil L1 of the transformer 322. The switch is controlled by the controller 126 to cause an alternating current signal of a desired duty cycle across the primary coil L1. The flyback transformer 322 steps up the voltage to a higher voltage a.c. signal at the output (secondary coil L2) of the transformer. A diode 318 coupled to the secondary coil L2 of the transformer 322 rectifies the a.c. signal generated at the secondary coil L2, resulting in a series of positive current pulses being generated by the HV charger circuit 202. The charge capacitor 204 is coupled across the output of the HV charger circuit 202 to be charged during defibrillation and to be used as a filter capacitor during pacing. The charge delivery switch 206 connects the charge capacitor 204 to electrodes 122A and 122B in response to one or more shock control signals 210 generated by the controller 126 (FIG. 2). In the embodiment illustrated in FIG. 3, the charge delivery switch 206 is implemented as an H-bridge electrically coupling the charge capacitor 204 to electrodes 122A and 122B.

In alternative embodiments of the present invention, alternative designs for the charge delivery switch 206 can be used. The H-bridge in the illustrated embodiment includes switches 302, 304, 310 and 312 to control the electrical connection between the charge capacitor 204 and the electrodes 122A and 122B. It should be understood that the H-bridge of the charge delivery switch 206 can be controlled to apply, for example, monophasic or biphasic defibrillation pulses to the electrodes 122.

The positive current pulses that are generated by the HV energy circuit 202 can be used to charge the capacitor 204 to a high voltage level prior to discharge or to provide a substantially steady flow of current where positive current pulses are continuously applied to the charge capacitor 204, as is known in the art. Charging of the capacitor to a high voltage level by the HV charger circuit 202 is performed for delivery of defibrillating energy to a patient. The HV charger circuit 202 can also be used to provide a pacing current, with the charge capacitor 204 then acting as a filter capacitor. When providing a pacing current, the controller 126 controls the current output of the HV energy circuit 202 by adjusting the duty cycle of the current pulses applied across the primary coil L1 of the transformer 322 based on the magnitude of the sense signal 214 provided to the controller by the measurement circuit 212. The measurement circuit 212 includes a pair of series coupled resistors 330, 332, and a MOSFET switch 340 coupled in parallel between the charge capacitor 204 and the charge delivery switch 206. The switch 340 is shown in FIG. 3 as being a FET device having a diode coupled across the source and drain of the FET. However, alternative switch designs can be used without departing from the scope of the present invention. The resistors 330 and 332 provide a minimum load across the FET device and a current sense resistor, respectively, for the measurement circuit. Since the measurement circuit 212 only needs to be active during pacing when low voltage pacing current is produced, the measurement circuit can advantageously be constructed with entirely low voltage components.

During the application of defibrillating energy, the controller 126 activates the switch 340 to bypass the resistors 330, 332. However, during the application of pacing current, the controller opens the switch 340, forcing return current to flow through the resistors 330, 332 for sensing. A voltage measurement is made at a measurement node 334 to provide the controller 126 with a value that can be used to calculate the magnitude of the pacing current delivered to a patient. As previously discussed, based on the measurement, the controller 126 can control the power source control 324 to adjust the duty cycle of the drive signal for the flyback transformer and hence the output current of the HV charger circuit 202.

In operation, after determining that a defibrillating pulse should be delivered to a patient, the charge capacitor 204 is charged to a high voltage that is sufficient to deliver an adequate level of defibrillation energy. The defibrillating energy can be delivered in the form of monophasic or biphasic pulses. As previously mentioned, the embodiment of the charge delivery switch 206 illustrated in FIG. 3 can be controlled by the controller 126 to apply monophasic or biphasic defibrillation pulses to the electrodes 122A and 122B. For example, to apply a biphasic pulse from the charge capacitor 204 to the electrodes 122A and 122B, the switches 302 and 312 are closed and switches 304 and 310 are opened. This connects the electrode 122A to the charge capacitor 204 and the electrode 122B to ground. Then, to reverse the polarity of the defibrillation pulse, the switches 302 and 312 are opened and the switches 304 and 310 are closed to connect the electrode 122A to ground and the electrode 122B to the charge capacitor 204.

When the defibrillator 100 is used for delivering pacing current, the controller opens the switch 340 so that the controller 126 can determine the voltage dropped across sense resistor 332 and hence the magnitude of pacing current delivered to a patient (the patient impedance), and the switches 302 and 312 are closed and the switches 304 and 310 are opened to allow current to be delivered across the patient in one direction. The controller 126 further controls the power source control 324 so that the current pulses output by the IV charger circuit 202 are sufficient to provide adequate pacing current. The charge capacitor 204 behaves as a filter capacitor to smooth the pulsed current output by the IV charger circuit 202. As the substantially DC pacing current is delivered to the patient, the magnitude of the current is monitored by the controller 126 using the measurement circuit 212. In the event that the magnitude of the pacing current delivered to the patient is more or less than adequate, the controller 126 controls the duty cycle of the power source control 324 to adjust the pulsed current output by the HV energy circuit 202 accordingly. For a low patient impedance, a low duty cycle is used to produce low pacing current, and for a higher patient impedance a higher duty cycle is used to produce higher pacing current. In effect, the circuitry used for defibrillation is augmented by the low voltage measurement circuit 212 and appropriate control software in the controller 126 in order to provide the pacing function.

In the embodiment shown in FIG. 3, the charge delivery switch 206 can be used to reverse pacing current as well, and thereby reduce any offset voltage induced in the electrodes 122A and B. For example, a high energy, short duration pacing pulse can be delivered in one direction by turning on switching elements 302 and 312, and thereafter a second pacing pulse which is lower in voltage and longer in duration can be delivered in the opposite direction by turning on switching elements 304 and 310. The pacing current waveform can be bipolar or biphasic as desired.

The invention claimed is:
1. A defibrillator adapted to selectively provide defibrillation pulses in a defibrillation mode and pacing pulses in a pacing mode, comprising:
 patient electrodes;
 a power source for providing power;
 an energy delivery system coupled to the power source and the electrodes,
 having;
  a controllable charging circuit coupled to the power source and configured to generate electrical energy and current pulses, and
  a capacitance storage circuit coupled to the charging circuit, for storing the electrical energy and for filtering the current pulses,
 the energy delivery system configured to generate electrical energy, store the electrical energy in the storage circuit, and couple the stored electrical energy to the patient electrodes to deliver the defibrillation pulses in the defibrillation mode, and further configured to generate current pulses and couple the current pulses to the patient electrodes via the storage circuit to deliver the current pulses as pacing pulses in the pacing mode; and
 a controller coupled to the energy delivery system, having
  a measuring circuit responsive to pacing pulses delivered during the pacing mode for producing a pacing control signal, including sensing resistors and a switch coupled in parallel between the capacitance storage circuit and the patient electrodes; and
  a control circuit responsive to the pacing control signal and coupled to the charging circuit to control the charging circuit to produce a pacing current in the pacing mode, wherein
 the controller closes the measuring circuit switch to bypass the sensing resistors during the defibrillation mode.

2. The defibrillator of claim 1 wherein the capacitance storage circuit is operable to filter the current pulses in the pacing mode.

3. The defibrillator of claim 1 wherein the control circuit acts to control the duty cycle of the charging circuit.

4. The defibrillator of claim 3 wherein the control circuit includes a transformer responsive to an input signal for producing an output signal,
 wherein the control circuit acts to control the duty cycle of the transformer.

5. The defibrillator of claim 1 wherein the measuring circuit includes a sensing resistor coupled to the capacitance storage circuit for developing the pacing control signal as a measure of the pacing current delivered during the pacing mode.

6. The defibrillator of claim 1, wherein the control circuit further comprises a software program, responsive to the pacing control signal, for determining a charge control signal during the pacing mode.

7. The defibrillator of claim 1, wherein the measuring circuit comprises a circuit of entirely low voltage components.

8. The defibrillator of claim 1, wherein the charging circuit is operable to charge the capacitance storage circuit to a defibrillation voltage level in excess of 1000 volts in the defibrillation mode and is controlled to charge the capacitance storage circuit to a voltage below 1000 volts in the pacing mode.

9. The defibrillator of claim 1 wherein the power source comprises a battery.

10. The defibrillator of claim 1 wherein the energy delivery system comprises:

an output circuit coupled to the patient electrodes and the capacitance storage circuit, the output circuit configured to deliver the energy stored by the capacitance storage circuit as defibrillating pulses and to deliver the current pulses filtered by the capacitance storage circuit as pacing pulses.

11. The defibrillator of claim 1 wherein the controllable charging circuit includes a switched mode power supply having a flyback transformer.

12. The defibrillator of claim 11, wherein the controller is responsive to the magnitude of the delivered pacing pulses for controlling the operation of the flyback transformer.

13. The defibrillator of claim 12, wherein the controller is responsive to the magnitude of the delivered pacing pulses for controlling the duty cycle of the input signal of the flyback transformer.

14. The defibrillator of claim 1 wherein the output circuit is configured to deliver the energy stored in the defibrillation mode as a biphasic pulse.

15. The defibrillator of claim 10, wherein the measuring circuit is coupled to the output circuit to generate an output signal having a magnitude indicative of the magnitude of the pacing pulses delivered.

16. The defibrillator of claim 15 wherein the measuring circuit comprises a circuit of low voltage components.

17. A method for delivering defibrillation pulses or pacing pulses to a patient from the defibrillator of claim 1, comprising:

charging the storage circuit to a defibrillation voltage level in the defibrillation mode;

delivering defibrillating energy stored by the storage circuit to the patient in the defibrillating mode;

monitoring the pacing pulses delivered to the patient in the pacing mode; and controlling, on the basis of the monitored pacing pulses, the production of pacing pulses of a switched mode power supply in the pacing mode to produce pacing pulses.

18. The method of claim 17 wherein controlling further comprises controlling the duty cycle at which the power supply is switched to produce a desired pacing pulse.

* * * * *